(12) United States Patent
Effenberger et al.

(10) Patent No.: US 6,319,697 B1
(45) Date of Patent: Nov. 20, 2001

(54) (S)-HYDROXYNITRILE LYASES WITH IMPROVED SUBSTRATE ACCEPTANCE AND THEIR USE

(75) Inventors: Franz Effenberger, Stuttgart; Harald Wajant, Leinfelden-Echterdingen; Peter Lauble, Berlin; Siegfried Förster, Stuttgart; Holger Buhler, Ludwigsburg, all of (DE); Helmut Schwab, Graz (AT); Christoph Kratky, Graz (AT); Ulrike Wagner, Graz (AT); Ernst Steiner, Tobelbad (AT)

(73) Assignee: DSM Fine Chemicals Austria GmbH, Linz (AT)

( * ) Notice: Subject to any disclaimer, the term of this patent is extended or adjusted under 35 U.S.C. 154(b) by 0 days.

(21) Appl. No.: 09/345,773

(22) Filed: Jul. 1, 1999

(30) Foreign Application Priority Data

Jul. 2, 1998 (AT) .................................................. 1159/98

(51) Int. Cl.⁷ ....................................................... C12P 13/00
(52) U.S. Cl. ............................................ 435/128; 435/232
(58) Field of Search ...................................... 435/232, 128

(56) References Cited

U.S. PATENT DOCUMENTS 5,346,816   9/1994   Griengl et al. ........................ 435/128

FOREIGN PATENT DOCUMENTS

WO97/03204   1/1997 (WO).

OTHER PUBLICATIONS

GenBank Accession No. AAC49184 (Mar. 1996).*
GenBank Accession No. S45682 (Dec. 1994).*
Wajant et al. Identification of Potential Active–Site Residues in the Hydroxynitrile Lyase from *Manihot esculenta* by Site–Directed Mutagenesis. J. Biol. Chem. (1996) 271(42): 25830–25834.*
Hasslacher et al. Molecular CLoning of the Full–Length cDNA of (S)Hydroxynitrile Lyase from *Hevea brasiliensis*. J. Biol. Chem. (1996) 271(10): 5884–5891.*
Wilke–Mounts e tal. Tryptophan–Free *Escherichia coli* F1–ATpase. Archives of Biochemistry and Biophysics (1994) 309(2): 363–368.*

* cited by examiner

*Primary Examiner*—Ponnathapu Achutamurthy
*Assistant Examiner*—Kathleen Kerr
(74) *Attorney, Agent, or Firm*—Wenderoth, Lind & Ponack, L.L.P.

(57) ABSTRACT

(S)-Hydroxynitrile lyases which have an improved substrate acceptance and which are derived from the *Hevea brasiliensis* and *Manihot esculenta* (S)-hydroxynitrile lyases, wherein one or more bulky amino acid residues within the hydrophobic channel leading to the active center have been replaced with less bulky amino acid residues.

13 Claims, No Drawings

SEQUENCE LISTING

<160> NUMBER OF SEQ ID NOS: 7

<210> SEQ ID NO 1
<211> LENGTH: 37
<212> TYPE: DNA
<213> ORGANISM: OLIGONUCLEOTIDE

<400> SEQUENCE: 1

```
gctcatggag gtgtttccgg acgcaaaaga caccacg                        37

<210> SEQ ID NO 2
<211> LENGTH: 38
<212> TYPE: DNA
<213> ORGANISM: OLIGONUCLEOTIDE

<400> SEQUENCE: 2
cgtggtgtct tttgcgtccg gaaacacctc ccatgagc                       38

<210> SEQ ID NO 3
<211> LENGTH: 37
<212> TYPE: DNA
<213> ORGANISM: OLIGONUCLEOTIDE

<400> SEQUENCE: 3
gctcatggag gtgtttccgg acttcaaaga caccacg                        37

<210> SEQ ID NO 4
<211> LENGTH: 38
<212> TYPE: DNA
<213> ORGANISM: OLIGONUCLEOTIDE

<400> SEQUENCE: 4
cgtggtgtct ttgaagtccg gaaacacctc ccatgagc                       38

<210> SEQ ID NO 5
<211> LENGTH: 21
<212> TYPE: DNA
<213> ORGANISM: PCR PRIMER

<400> SEQUENCE: 5
gactggttcc aattgacaag c                                         21

<210> SEQ ID NO 6
<211> LENGTH: 21
<212> TYPE: DNA
<213> ORGANISM: PCR PRIMER

<400> SEQUENCE: 6
gcaaatggca ttctgacatc c                                         21

<210> SEQ ID NO 7
<211> LENGTH: 53
<212> TYPE: DNA
<213> ORGANISM: PCR PRIMER

<400> SEQUENCE: 7
aagcttttgg agtcgtttcc tgacgcgaga gacacagagt attttacgtt cac       53
```

(S)-HYDROXYNITRILE LYASES WITH IMPROVED SUBSTRATE ACCEPTANCE AND THEIR USE

BACKGROUND OF THE INVENTION

1. Field of the Invention

The invention relates to (S)-hydroxynitrile lyases which have an altered substrate Acceptance.

2. Description of the Related Art

The implementation of chemical reactions with the aid of biological catalysts is gaining increasing importance, especially in those areas of application in which use can be made of the property, which is frequently pronounced in enzymes, are preferentially transforming one of the two enantiomers in reactions using chiral or prochiral components.

This group of enzymes includes the hydroxynitrile lyase (HNL) family, inter alia *Hevea brasiliensis* HNL (HbHNL) and *Manihot esculenta* HNL (MeHNL). The two enzymes exhibit a high sequence identity and belong to the proteins of the "α/β-hydrolase fold" type, which exhibit a characteristic tertiary fold and a so-called catalytic triad containing aspartic acid, serine and histidine as the active center. In this context, the active center is located at the inner end of a hydrophobic channel. In principle, HbHNL and MeHNL are suitable for converting a large number of carbonyl compounds, such as aliphatic, alicyclic, unsaturated, aromatic and heteroaromatic aldehydes and ketones, into the corresponding (S)-cyanohydrins. Since HNLs are gaining ever greater importance as biocatalysts for preparing (S)-cyanohydrins, attempts are constantly being made to improve their catalytic activity and substrate acceptance. The substrate acceptance of the HNLs which have so far been available is not satisfactory, particularly in the case of starting compounds possessing bulky residues, as a result of which the corresponding cyanohydrins are obtained either at a low conversion rate and/or in low enantiomeric excess.

The object of the invention was consequently to provide (S)-hydroxynitrile lyases having an improved substrate acceptance.

SUMMARY OF THE INVENTION

The invention consequently relates to (S)-hydroxynitrile lyases which have an altered substrate acceptance, in particular a substrate acceptance which is improved in the case of defined substrates, and which are derived from the (S)-hydroxynitrile lyases obtained from *Hevea brasiliensis* and *Manihot esculenta*, wherein one or more bulky amino acid residues within the hydrophobic channel leading to the active center are replaced by less bulky amino acid residues.

DESCRIPTION OF THE PREPARED EMBODIMENTS

The HNLs according to the invention are mutants of *Hevea brasiliensis* (HbHNL) or *Manihot esculenta* (MeHNL) (S)-HNLs which can be obtained from recombinantly modified microorganisms such as *Pichia pastoris, Saccharomyces cerevisiae* or *Escherichia coli* (WO 97/03204). In this context, the recombinant HNLs which are to be modified can also possess a truncated sequence, which is obtained, for example, by removing the first amino acid(s) in sequence. The mutants possess an altered sequence of those amino acids which form the hydrophobic channel which leads to the active center.

In this context, individual bulky amino acid residues, or several bulky amino acid residues, are replaced by less bulky amino acid residues. Preference is given to replacing tryptophan, as a bulky amino acid residue, with a less bulky amino acid residue such as alanine, glycine, valine or phenylalanine. Particular preference is given to mutants in which the tryptophan at position 128 of the full-length sequence of HbHNL or MeHNL has been replaced by alanine or phenylalanine.

The HNLs according to the invention are prepared by being functionally overexpressed in recombinantly modified microorganisms such as *Pichia pastoris, Saccharomyces cerevisiae* or *Escherichia coli*, for example in analogy with M. Hasslacher et al., J. Biol. Chem. 1996, 271, 5884 or Wajant, H. and Pfizenmaier, K. 1996, J. Biol. Chem. 25830–24834. The mutation is carried out, for example, using a Quikchange™ Side-Directed Mutagenesis Kit (Stratagene) in accordance with the manufacturer's instructions. The Quikchange™ Side-Directed Mutagenesis Kit is a ready-to-use system for preparing specific mutants and is marketed, for example, by Stratagene Cloning Systems, La Jolla, Calif. (USA).

The resulting HNLs are purified by standard methods, for example in analogy with Wajant, H. Pfizenmaier, K., J. Biol Chem. 1996, 25830–25834.

The HNLs according to the invention are suitable for preparing (S)-cyanohydrins at a superior turnover rate and/or in a higher enantiomeric excess as compared with the state of the art. The HNLs according to the invention are employed, in particular, when aliphatic and aromatic aldehydes and ketones are used as substrates. In this context, aliphatic aldehydes are preferably to be understood as being saturated or unsaturated, branched or cyclic aldehydes having 2 to 20 C atoms.

Particular preference is given to saturated or unsaturated branched aldehydes having 4 to 18 C atoms. The aliphatic and aromatic aldehydes may be unsubstituted or substituted by groups which are inert under the reaction conditions, for example by optionally substituted aryl or heteroaryl groups, such as phenyl or indolyl groups, or by halogen, ether, alcohol, acyl, carboxylic acid, nitro or azido groups.

Examples of suitable aliphatic aldehydes are hexanal, hexenal, heptanal, propanal, octanal, octenal and 2-methylpropanal. Examples of suitable aromatic or heteroaromatic substrates are benzaldehyde or variously substituted benzaldehydes, such as 3-phenoxybenzaldehyde, 4-fluoro-3-phenoxybenzaldehyde, 2-chlorobenzaldehyde, 2-nitrobenzaldehyde, 4-methylbenzaldehyde, etc.

The substrates are reacted with a cyanide group donor in the presence of the HNLs according to the invention.

Suitable cyanide group donors are hydrocyanic acid, alkali metal cyanides or a cyanohydrin of the general formula $$R_1R_2C(OH)(CN) \qquad \text{formula I.}$$

In formula I, $R_1$ and $R_2$ denote, independently of each other, hydrogen or an unsubstituted hydrocarbon group, or $R_1$ and $R_2$ together denote an alkylene group having 4 or 5 C atoms, with $R_1$ and $R_2$ not simultaneously denoting hydrogen. The hydrocarbon groups are aliphatic or aromatic, preferably aliphatic groups. $R_1$ and $R_2$ preferably denote alkyl groups having 1–6 C atoms; the cyanide group donor is very preferably acetone cyanohydrin.

The cyanide group donor can be prepared using known methods. Cyanohydrins, in particular acetone cyanohydrin, can also be obtained commercially. Hydrocyanic acid (HCN), KCN, NaCN or acetone cyanohydrin is preferably used as the cyanide group donor, with hydrocyanic acid being particularly preferably used.

In this context, the hydrocyanic acid can also be released from one of its salts, such as NaCN or KCN, only shortly before the reaction and added to the reaction mixture as the substance itself or dissolved form.

The reaction can be carried out in an organic, aqueous or 2-phase system or in an emulsion. The aqueous system used is an aqueous solution or buffer solution which contains the HNL according to the invention. Examples of these solutions or buffer solutions are Na citrate buffer, phosphate buffer, etc.

The organic diluents employed can be aliphatic or aromatic hydrocarbons which are not miscible, or only slightly miscible, with water and which are optionally halogenated, alcohols, ethers or esters, or mixtures thereof. Methyl tert-butyl ether (MTBE), diisopropyl ether, dibutyl ether or ethyl acetate, or a mixture of these compounds, is preferably employed. In this context, the HNLs according to the invention can be present in the organic diluent either as such or immobilized; however, the reaction can also take place in a two-phase system or in an emulsion using non-immobilized HNL.

EXAMPLE 1

Preparation of HbHNL Which is Mutated at Position 128

Specific mutants were prepared using the QuikChange™ Site-Directed Mutagenesis Kit (Stratagene Cloning Systems, La Jolla, Calif., USA). Apart from an amino acid exchange in position 128 of the HNL protein, a cleavage site for the restriction enzyme AccIII was additionally introduced by way of a silent mutation.

The following oligonucleotides were used for this purpose:

a) For preparing the mutant W128A: W128AFOR: 5' GCTCATGGAGGTGTTTCCGGACGCAAAAGACACCACG 3' (SEQ. ID NO:1) W128AREV: 5' CGTGGTGTCTTTTGCGTCCGGAAACACCTCCCATGAGC 3' (SEQ. ID NO:2)

b) For preparing the mutant W128F: W128FFOR: 5' GCTCATGGAGGTGTTTCCGGACTTCAAAGACACCACG 3' (SEQ. ID NO:3) W128FREV: 5' CGTGGTGTCTTTGAAGTCCGGAAACACCTCCCATGAGC 3' (SEQ. ID NO:4)

The recombinant plasmid pHNL104, which contains the cDNA of the *Hevea brasiliensis* hnl gene, was used as the template for the Mutagenesis reaction (plasmid preparation in analogy with Hasslacher et al. 1996 J. Biol. Chem. 271, 5884). The mutated plasmid was then transformed into *Escherichia coli* (*Epicurian Coli®* XL1 blue supercompetent cells, Stratagene Cloning Systems, La Jolla, Calif., USA).

The plasmid DNA was then isolated from several transformants and examined with the restriction enzyme AccIII for the presence of the AccIII cleavage site which was introduced together with the mutation. Positive clones were then subjected to a sequence analysis in the region of the hnl cDNA in order to verify the presence of the desired mutation at position 128 and in order to be able to exclude the possibility that unwanted mutations had been introduced in other regions of the hnl gene. A fragment, which encodes the respective mutated HNL, was then isolated from the corresponding plasmid by means of digestion with the restriction endonuclease EcoRI and subsequent agarose gel electrophoresis. This fragment was ligated into the DNA of the expression vector pHIL-D2 (Invitrogen Corporation, Carlsbad, Calif., USA), which DNA had been linearized with EcoRI and dephosphorylated with alkaline phosphatase, and the recombinant DNA was transformed into *Escherichia coli* SURE® (Stratagene Cloning Systems, La Jolla, Calif., USA). The plasmid DNA was once again prepared from several transformants and examined using the restriction endonuclease NdeI for the presence and/or the orientation of the hnl cDNA with regard to the aoxI promoter of pHIL-D2. Plasmid DNA from suitable clones was then linearized with the restriction enzyme NotI and subsequently introduced, by means of electrotransformation, into the *Pichia pastoris* strain GS115, with selection being carried out for complementation of the histidine auxotrophy of the host strain employed. Transformants which were thus obtained were subsequently tested for reduced growth on minimal methanol medium. Several such Mut$^s$ transformants were then tested with regard to their ability to express HNL protein, and a suitable expression strain was selected for each of the two HNL mutants. This work was carried out in analogy with the experiments which are described in detail in the manual which accompanies the Pichia Expression Kit (Invitrogen Corporation, Carlsbad, Calif., USA).

The integration of the hnl cDNA into the *Pichia pastoris* genome, and the presence of the specific mutation in the two expression strains, were checked by sequencing a DNA fragment which had been amplified by PCR. Chromosomal DNA, which was isolated using the method described in Ausubel et al., Current Protocols in Molecular Biology, Vols. 1–3, Greene Publishing Associates and Wiley-Interscience, N.Y., 1995, served as the template for the PCR. The sequences of the PCR primers were as follows:

PP5AOX1 5' GACTGGTTCCAATTGACAAGC 3' (SEQ. ID NO:5)

PP3AOX1 5' GCAAATGGCATTCTGACATCC 3' (SEQ. ID NO:6)

The expression strains were fermented, and the mutated HNL proteins were isolated and purified, as described in Hasslacher et al., 1997, Protein Expression and Purification, 11, 61–71.

EXAMPLE 2

Preparation of MeHNL Which is Mutated in Position 128.

The mutation was transformed into pQE4-MeHNLwt using the Quick-Change Sited-Directed Mutagenesis Kit (Stratagene Cloning Systems, La Jolla, Calif., USA). For this, 2 complementary primers, which correspond to nucleotides 383–435 of MeHNL:5' AAG CTT TTG GAG TCG TTT CCT GAC GCG AGA GAC ACA GAG TAT TTT ACG TTC AC 3' (SEQ. ID NO:7) and which contain the desired mutation (underlined), were extended using Pfu DNA polymerase, and the resulting product was treated with Dpnl. The mutated plasmids were then transformed into E.coli XL1 blue. The mutants were checked by sequence analysis using a modified determination method in analogy with Sanger et al., (1977) Proc. Natl. Acad. Sci. USA, 74, 5463–5467 and employing the T7DNA analysis system (Pharmacia).

EXAMPLE 3

Preparation of (S)-3-phenoxybenzaldehyde Cyanohydrin (S)-3-Phenoxybenzaldehyde cyanohydrin (PBAC) was obtained by reacting 10 or 5 mmol, respectively, of m-phenoxybenzaldehyde (PBA), and 14.4 or 7.7 mmol, respectively, of HCN in tert-butyl methyl ether (MTBE) in the presence of MeHNL W128A which was substituted with alanine in position 128 or of recombinant MeHNL (J. Hughes et al., Arch. Biochem. Biophys. 1994, 311(2), pp. 496–502) or of recombinant HbHNL—Ex. mutant. For this, in each case 1.3 ml of enzyme solution (0.26 ml in the case of HbHNL) were diluted with 8.3 ml of 50 mmol of Na citrate buffer, pH 5.4, (or 9.74 ml of dist. $H_2O$ in the case of HbHNL), after which the appropriate quantity of PBA (1.98 g1 g) and 3 or 1.5 ml of MTBE were added; 0.06 ml of HCN/ml of aldehyde was then rapidly added dropwise. The course of the reaction was followed by way of the decrease in the aldehyde content using IP in-process monitoring. The reactions were stopped after 2 hours. For working up, the reaction solutions were in each case diluted with 2.5 ml of MTBE, shaken and centrifuged.

The results are shown in Table 1.

TABLE 1

| HNL | IU/ml | mmol of PBA | Content of PBAC [%] | ee [%] |
|---|---|---|---|---|
| MeHNL (wild type) | 1092 | 10 | 82 | n.d. |
| MeHNL (wild type) | 1092 | 5 | 88.5 | 97.03 |
| MeHNL (W128A) | 315 | 10 | 98.7 | n.d. |
| MeHNL (W128A) | 315 | 5 | 97*) | 97 |
| HbHNL | 5200 | 10 | 83 | n.d. |
| HbHNL | 5200 | 5 | 84.5 | n.d. |

*)after 1.5 h
n.d. not determined

EXAMPLE 4

Comparison of Recombinant MeHNL (wild type) from Manihot Esculenta and Mutant MeHNL W128A in Organic Medium.

In analogy with Ex. 3, 3 mg of enzyme, 100 mg of nitrocellulose (pretreated with 20 mmol of citrate buffer, pH 3.3), 1 mmol of substrate and 150 µl of HCN were reacted in 5 ml of diisopropyl ether.

The results are shown in Table 2.

TABLE 2

| | MeHNL | | | W128A | | |
|---|---|---|---|---|---|---|
| Substrate | t [h] | Yield [%] | ee [%] | t [h] | Yield [%] | ee [%] |
| Nonanal | 6 | 35 | 81.1 | 6 | 87.3 | 80.2 |
| Heptanal | 1 | 99 | 80 | 1 | 99.5 | 88 |
| 2-Methyl-butanal | 4.5 | 89 | 93.6 | 4.5 | 99 | 96.6 |
| 2-Hexenal | 3.2 | 21.1 | >99 | 3.2 | 85 | 96 |
| n-PBA | 7 | 30 | 99 | 8 | 82 | 99 |
| p-HBA | 2 | 31 | >99 | 2 | 60 | >99 |
| CPA | 1 | 90.7 | 99 | 1 | 94.3 | 99 |
| PPA | 0.3 | 79 | 67 | 0.3 | 93 | 86 |
| Phenyl-acetone | 4 | 69.8 | 99 | 4 | 81.6 | 96 |
| BMK | 4.5 | 100 | 52 | 4.5 | 100 | 78 |
| BEK | 5 | 40 | 45 | 5 | 46 | 82 | p-HBA p-Hydroxybenzaldehyde
PPA Phenylpropionaldehyde
CPA Cyclopenten-1-ylacetaldehyde
BMK Butyl methyl ketone
BEK Butyl ethyl ketone

EXAMPLE 5

Comparison of Recombinant MeHNL and Mutant MeHNL W128A in an Aqueous Buffer System In analogy with Ex. 3, 1.2 mg of enzyme together with 0.5 mmol of substrate in 2.5 ml of a 0.5 M Na citrate buffer, pH 3.8, were reacted with 1 mmol of KCN in 3.5 ml of 0.5 M Na citrate buffer, pH 3.8.

The results are shown in Table 3.

TABLE 3

| | MeHNL | | | W128A | | |
|---|---|---|---|---|---|---|
| Substrate | t [h] | Yield [%] | ee [%] | t [h] | Yield [%] | ee [%] |
| FPBA | 4 | 11 | 99 | 4 | 47 | 95 |
| PBA | 22 | 66 | 97 | 22 | 75 | 92 |
| m-HBA | 3 | 74 | 0 | 3 | 80 | 0 |
| p-HBA | 1 | 76 | 92 | 1 | 71 | 96 |
| PPA | 1.2 | 60 | 21 | 1.2 | 94 | 90 |

FPBA 4-Fluoro-3-phenoxybenzaldehyde

What is claimed is:

1. An (S)-hydroxynitrile lyase obtained from *Hevea brasiliensis* or *Manihot esculenta* which (1) comprises a hydrophobic channel leading to an active center, (2) has one or more tryptophan residues within said hydrophobic channel replaced with alanine, glycine, valine or phenylalanine, and (3) has a higher percentage yield of cyanohydrin product than the wild-type (S)-hydroxynitrile lyase from substrates selected from the group consisting of aliphatic aldehydes, aromatic aldehydes and ketones.

2. The (S)-hydroxynitrile lyase as claimed in claim 1, wherein the amino acid sequence of the (S)-hydroxynitrile lyase is truncated and said (S)-hydroxynitrile lyase retains said higher percentage yield of (3).

3. The (S)-hydroxynitrile lyase as claimed in claim 1 wherein the amino acid sequence of the (S)-hydroxynitrile lyase is full-length.

4. The (S)-hydroxynitrile lyase as claimed in claim 3, wherein the full-length amino acid sequence of (S)-hydroxynitrile lyase is from *Hevea brasiliensis*.

5. The (S)-hydroxynitrile lyase as claimed in claim 3, wherein the full-length amino acid sequence of (S)-hydroxynitrile lyase is from *Manihot esculenta*.

6. The (S)-hydroxynitrile lyase as claimed in claim 1, wherein said one or more tryptophan residues is/are replaced with alanine or phenylalanine.

7. The (S)-hydroxynitrile lyase as claimed in claim 1, wherein one of said tryptophan residue is replaced with alanine or phenylalanine by site-directed mutagenesis using a primer pair selected from the group consisting of (a) SEQ ID Nos: 1 and 2, and (b) SEQ ID Nos: 3 and 4.

8. The (S)-hydroxynitrile lyase as claimed in claim 7, wherein the amino acid sequence of the (S)-hydroxynitrile lyase is full-length and is from *Hevea brasiliensis*.

9. The (S)-hydroxynitrile lyase as claimed in claim 1, wherein one of said tryptophan residue is replaced with alanine by site-directed mutagenesis using two complementary primers which correspond to the nucleotide sequence of SEQ ID No. 7.

10. The (S)-hydroxynitrile lyase as claimed in claim 9, wherein the amino acid sequence of the (S)-hydroxynitrile lyase is full-length and is from *Manihot esculenta*.

11. The (S)-hydroxynitrile lyase as claimed in claim 1, wherein said aliphatic aldehyde is a saturated or unsaturated, branched or cyclic aldehyde having 2 to 20 carbon atoms.

12. The (S)-hydroxynitrile lyase as claimed in claim 11, wherein said aliphatic aldehyde is a saturated or unsaturated, branched aldehyde having 4 to 18 carbon atoms.

13. A process for preparing (S)-cyanohydrins, which comprises reacting aliphatic and aromatic aldehydes and ketones, in the presence of a cyanide group donor, with the (S)-hydroxynitrile lyase as claimed in claim 1.

* * * * *